United States Patent [19]

Sullivan

[11] Patent Number: 4,965,540
[45] Date of Patent: Oct. 23, 1990

[54] MICROWAVE RESONANT CAVITY

[75] Inventor: James J. Sullivan, New Castle County, Del.

[73] Assignee: Hewlett-Packard Company, Palo Alto, Calif.

[21] Appl. No.: 345,813

[22] Filed: May 1, 1989

Related U.S. Application Data

[63] Continuation-in-part of Ser. No. 137,304, Dec. 23, 1987, abandoned.

[51] Int. Cl.$^5$ .............................. H01P 7/06; H01P 1/14
[52] U.S. Cl. ........................................ 333/227; 333/13; 333/99 PL
[58] Field of Search ............... 333/227, 230, 231, 222, 333/99 PL, 13, 17.2; 315/39, 39.53

[56] References Cited

U.S. PATENT DOCUMENTS

| | | | |
|---|---|---|---|
| 2,745,072 | 5/1956 | Golstein et al. | 333/99 P L |
| 3,374,393 | 3/1968 | Bramley | 315/39 |
| 3,493,805 | 2/1970 | Bass | 315/248 X |
| 3,602,837 | 8/1971 | Goldsborough | 333/99 P |
| 3,685,911 | 8/1972 | Dahlquist et al. | 356/86 |
| 3,705,319 | 12/1972 | Goldie et al. | 333/13 X |
| 4,395,684 | 7/1983 | Goldie et al. | 333/13 |
| 4,473,736 | 9/1984 | Bloyet et al. | 315/111.21 X |
| 4,575,692 | 3/1986 | Goldie | 333/13 |
| 4,654,504 | 3/1987 | Sullivan et al. | 219/121.48 |

OTHER PUBLICATIONS

L. G. Matus et al., "Tuning and Matching the TM$_{010}$ Cavity" Rev. Sci. Instrum. 54 (12), Dec. 1983, pp. 1667–1673.
M. R. Brown et al., "Reentrant Cavity As a Low-Power Plasma Source", Rev. Sci. Instrum. 57 (12), Dec. 1986, pp. 2957–2960.
Peter C. Uden, "Element-Selective Chromatographic Detection by Atomic Emission Spectroscopy", Chromography Forum, Nov.-Dec. 1986, pp. 17–26.
David L. Haas et al., "An Internally Tuned TM$_{010}$ Microwave Resonant Cavity for Moderate Power Microwave-Inducted Plasma", vol. 37, No. 1, 1983, Applied Spectroscopy, pp. 82–85.
Technical Note, Spectrochimica Acta, vol. 31B, pp. 483–486, 1976.
Hall and Parzen, "Measurement of Resonant-Cavity Characteristics", Proceedings of the I.R.E., Dec. 1953, pp. 1769–1773.
R. D. Satzger et al., "Detection of Halogens as Positive Ions Using A He Microwave Induced Plasma As An Ion Source for Mass Spectrometry", Spectrochimica Acta, vol. 42B, No. 5, 1987, pp. 705–712.

Primary Examiner—Eugene R. LaRoche
Assistant Examiner—Seung Hain
Attorney, Agent, or Firm—Richard F. Schuette

[57] ABSTRACT

A microwave resonant cavity for a spectroscopic light source includes a housing having therein a chamber formed by side walls and a cylindrical outer wall. The side walls having aligned openings therethrough which are on the longitudinal axis of the outer wall. A refractory tube which is adapted to contain a gaseous plasma extends through the aligned openings and across the chamber in the housing. The portion of the side walls of the chamber adjacent the openings are closer together than the remaining portions of the side walls so that the chamber has a first portion around the refractory tube which is narrower than a second portion of the chamber around the first portion. A coupling loop is electrically coupled to a side wall of the chamber within the second portion of the chamber and is connector to a coaxial connector which extends through the outer wall of the housing to deliver microwave power to the chamber. This provides a resonant cavity in which the plasma formed in the refractory tube is very short for increased power and greater brightness of the plasma. This also provides a resonant cavity which requires no tuning and is more stable.

30 Claims, 4 Drawing Sheets

MICROWAVE RESONANT CAVITY

RELATED APPLICATIONS

This is a continuation-in-part of my application Ser. No. 137,304, filed Dec. 23, 1987, entitled MICROWAVE RESONANT CAVITY.

FIELD OF THE INVENTION

The present invention relates to a microwave resonant cavity, and, more particularly, to a microwave resonant cavity for a spectroscopic device, such as for an optical spectroscopic device or a mass spectroscopic device.

BACKGROUND OF THE INVENTION

In the field of atomic emission spectroscopy, a gaseous plasma containing the atoms to be examined or measured, is used to excite the atoms sufficiently to cause the atoms to emit radiation at selected wavelengths. In plasma mass spectrometry, the excited atoms are fed into a system for analyzing the atoms electrically. One such device is shown and described in an article by R. D. Satzger et al, entitled "Detection of halogens as positive ions using a He microwave induced plasma as an ion source for mass spectrometry", published in SPECTROCHIMICA ACTA., Vol 42B, No. 5, 1987, pages 705–712. One device commonly used in this field is a microwave induced plasma which generally includes a refractory tube placed along the longitudinal axis of a resonant microwave cavity. A gas, such as helium, containing the atoms is fed into one end of the tube and is excited by the microwave energy supplied to the cavity. For optical spectrometry, the light generated by the atoms is emitted axially from the other end of the tube where it can be examined. For mass spectrometry, the excited atoms are drawn into the mass analyzer where it is examined electronically. A coaxial cable brings power from a microwave supply, generally a magnetron power tube, to the cavity. There is generally a tuner, either in series with the cable, or incorporated into the structure of the cavity. One type of cavity commonly used is shown and described in the Technical Note written by C.I.M. Beenakker, entitled "A cavity for microwave-induced plasmas operated in helium and argon at atmospheric pressure", published in SPECTROCHIMICA ACTA, Vol. 31B, pages 483–486, 1976.

There are several problems with the above described cavity. Both the plasma and the magnetron, can be, under certain circumstances, negative resistance devices. It is common for the tuning to be a critical adjustment, with different settings required for initiating a plasma and for running stably. It is common for tuning adjustments to be necessary after changes in the gas flow. If tuning is slightly in error, several problems can occur. Much of the power can be wasted, by being reflected back to the magnetron. Oscillations in power level can occur, either synchronized with the frequency of the filament power supply (usually 60 Hz) or a super-regenerative oscillation at any frequency from the audio range up to as high as 100 MHz. The system can jump erratically between different magnetron modes, leading to step changes in power. All of these problems lead to errors in measurement.

In cases of more serious mis-tuning, the plasma has a tendency to go out, or not to light at all. Also, large fractions of the power can be dissipated in auxiliary devices, such as tuners and coaxial connectors. In some cases, these devices can be destroyed, either by overheating, or by arcing. Even with apparently optimal tuning, it has been observed that there is substantial heat dissipation in the cables and tuners used with the microwave induced plasma devices. This implies that much of the microwave power is not well coupled into the plasma.

One type of resonant cavity known to those skilled in the art is sometimes referred to as a "coaxial reentrant cavity". The simple use of this cavity shape has not been sufficient to allow independence from the need for tuning. For instance, U.S. Pat. No. 4,575,692 to H. Goldie describes a coaxial reentrant cavity used to support a plasma discharge in a refractory tube. However, since there is still a potential problem with frequency drift, it was necessary to incorporate the cavity into the power-source circuitry, as the main frequency-determining element.

Many attempts have been made, some successful, to ameliorate some of the above problems. However, they have required complex systems for adjusting the tuning and the power or specially built tuners which are more robust and easier to tune. Some workers, such as L. G. Matus, C. B. Boss and A. N. Riddle, REVIEW OF SCIENTIFIC INSTRUMENTS, vol. 54, page 1667 (1983), have removed the need for a separate tuner by the expedient of incorporating a tuning means in the structure of the cavity itself. Clearly, this expedient does not offer the advantage of not having to tune the plasma. Other workers have used thick coupling loops to advantage. But this improvement has not by itself offered freedom from the need for tuning. D. L. Haas, J. W. Carnahan and J. A. Caruso, APPLIED SPECTROSCOPY, vol. 37, page 82 (1982) have used a thick coupling loop, but only to facilitate the use of an internal tuning means. Therefore, it would be desirable to have a microwave induced plasma device which does not require a tuner and is more stable.

SUMMARY OF THE INVENTION

A resonant cavity for high frequency electromagnetic radiation used to excite a gaseous plasma includes a housing having spaced side walls and an outer wall. The walls form therein a cylindrical chamber having an axis extending through the side walls. The chamber has a first portion adjacent and around the axis which is narrower between the side walls than a second portion which is around the first portion. A refractory tube extends along the axis of the chamber and through the side walls. The tube is adapted to contain the gaseous plasma. Means is coupled to the inner surface of a wall of the housing within the second portion of the chamber for coupling a high frequency electromagnetic radiation into the cavity.

DETAILED DESCRIPTION OF PREFERRED EMBODIMENTS

Figure 1:
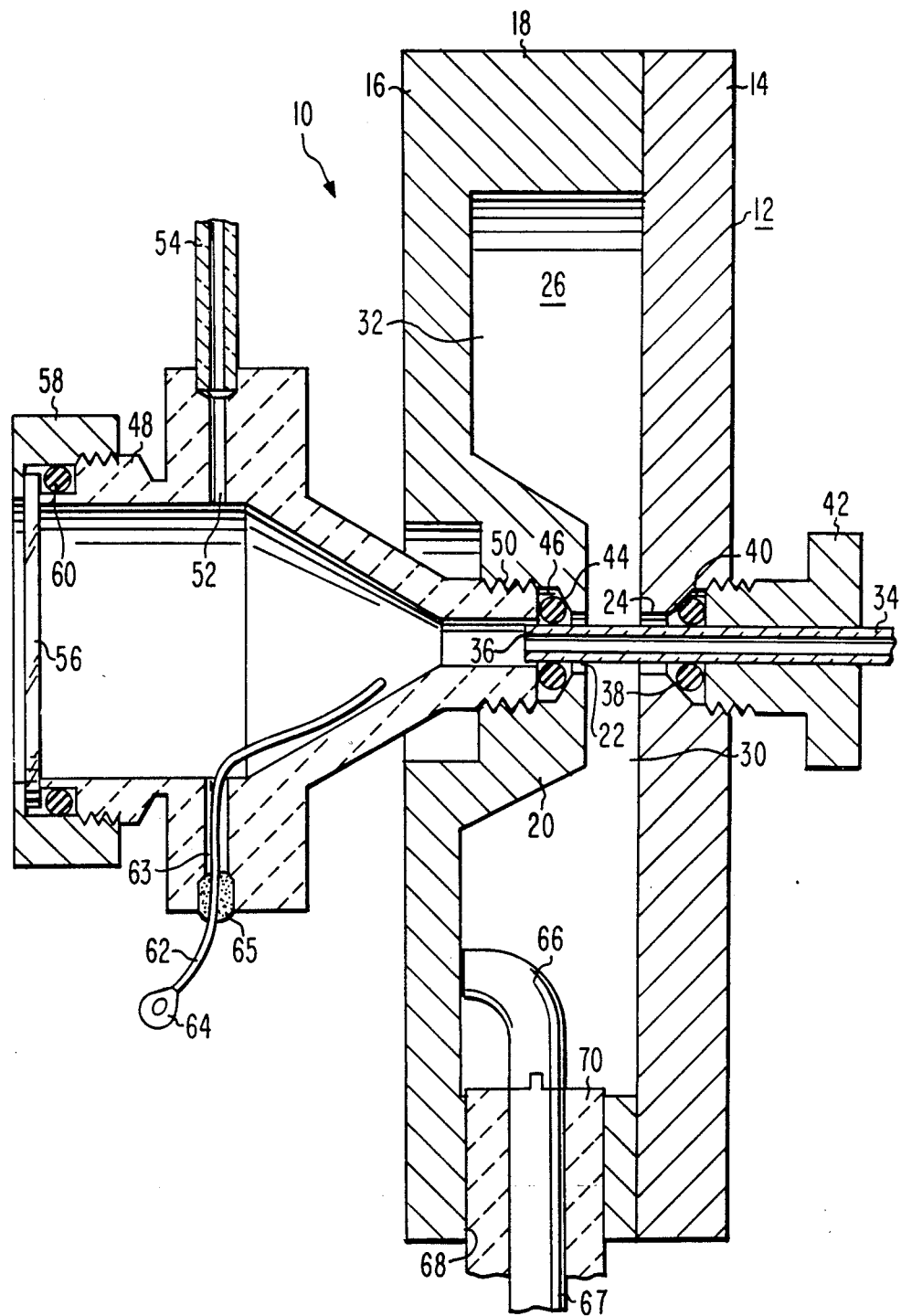
FIG. 1 is a sectional view of a form of the resonant cavity of the present invention for used in optical spectrometry.

Referring initially to FIG. 1, a form of a microwave cavity of the present invention is generally designated as 10. Microwave cavity 10 includes a housing 12 formed by a flat back plate 14, and a circular front plate 16. The front plate 16 has an annular flange 18 around its periphery which extends toward the back plate 14 and spaces the front plate 16 from the back plate 14. The front plate 16 has a substantially cylindrical hub 20 at its center which extends toward the back plate 14. The hub 20 has a central opening 22 therethrough, and the back plate 14 has an opening 24 therethrough in alignment with the opening 22 in the hub 20.

The back plate 14 and front plate 16 are made of a metal, such as copper, aluminum, brass or stainless steel, with the interior surfaces thereof having a highly smooth finish. The flange 18 on the front plate 16 engages the back plate 14 and is secured thereto in a manner to prevent leakage of microwave energy. This may be done by machining the interfacing surfaces smooth, and attaching the flange 18 to the back plate 14 with screws which are spaced much less than one quarter of the wavelength of the frequency used in the cavity. Alternatively, a microwave absorbing elastomeric seal can be provided between the flange 18 and the back plate 14.

The back plate 14 and front plate 16 form a chamber 26 therebetween which has a cylindrical outer wall formed by the flange 18 and side walls formed by the back plate 14 and front plate 16. The outer diameter of the cavity 26 is much larger than the width of the cavity 26 between the side walls. Along the longitudinal axis of the chamber 26 are the openings 22 and 24. Since the hub 20 projects from the front wall 16 toward the back wall 14, the chamber 26 has a first portion 30 adjacent and around its longitudinal axis which is narrower in width between the side walls of the chamber than the width of the remaining second portion 32 of the chamber 26 which surrounds the first portion 30. Preferably, the width of the first portion 30 of the chamber 26 is less than one-half the width of the second portion 32.

A refractory tube 34 extends through the openings 22 and 24 in the hub 20 and back plate 14 respectively, with one end 36 of the tube 34 being positioned within the hub 20. The other end of the tube 34, not shown, is connected to a source of the gas which forms the plasma. The tube 34 is made of a chemically resistance material with a high melting point, such as fused silica or alumina. A sealing ring 38 is in a recess 40 in the back plate 14 around the opening 24 and is held against the tube 34 by a nut 42 threaded in the recess 40. A sealing ring 44 is in a recess 46 around the opening 22 in the hub 20 and is pressed against the tube 34. Thus, the openings 24 and 22 around the tube 34 are sealed by the sealing rings 38 and 44. The sealing rings 38 and 44 may be made of an elastomeric material. However, for higher operating powers, the sealing rings 38 and 44 are preferably made of a material suited to high temperature operation, such as graphite.

An exhaust chamber 48 of an electrically insulating material, such as Teflon or a ceramic, is secured to the front plate 16. The exhaust chamber 48 is cylindrical and is tapered at one end to a connection 50 which is threaded into the recess 46 in the hub 20. The connection 50 engages the sealing ring 44 and compresses it against the tube 34. A gas exhaust opening 52 extends radially through the exhaust chamber 48 and has an exhaust tube 54 connected thereto. A glass window 56 which is transparent over the wavelength range of interest extends across the other end of the exhaust chamber 48 and is secured thereto by a threaded ring 58. For the UV-VIS region, fused silica has been found to be suitable for the window 56. A sealing ring 60 is provided between the glass window 56, the exhaust chamber 48 and the threaded ring 58 to seal the interface therebetween. An ignition wire 62 extends into the exhaust chamber 48 through an opening 63 therethrough. The end of the wire 62 within the exhaust chamber 48 is positioned near the end 36 of the refractory tube 34. The end of the wire 62 outside the exhaust chamber 48 has a connector 64 thereon by which the wire 62 can be connected to an ignition source, such as a tesla coil or an automobile ignition system. The space in the opening 63 around the wire 62 is sealed with a suitable sealing material 65, such as a cement.

Microwave power is coupled into the cavity 10 by a loop coupler utilizing a coupler 66 which is made as large in diameter as possible to minimize self-inductance. The coupler 66 is connected to a coaxial connector which includes a central conductor wire 67 extending through a hole 68 in the flange 18 of the front plate 16, and an insulator 70 between the conductor 67 and the hole 68. The coupling loop includes a current path from the coaxial connector, through the coupler 66, and a return path along the inside surface of the cavity. Thus, the conductor 67, insulator 70 and flange 18 form a section of a coaxial conductor of known impedance. If desired, the central conductor wire 67 may be integral with and an extension of the coupler 66.

The free end of the coupler 66 is terminated by abutting it against the inner surface of either the front plate 16, as shown in FIG. 1, or the back plate 14 within the second portion 32 of the chamber 26. This may be accomplished by an interference fit which makes a good electrical contact with the plate. However, a gap between the end of the coupler 66 and the plate that is sufficiently narrow can actually give better electrical performance, since the capacitance of the gap compensates for some of the undesired self inductance of the coupler 66. This means that if the contact between the coupler 66 and the plate fails, performance may actually improve.

The coaxial connector formed by conductor 67, insulator 70 and hole 68 could equally well be positioned on the inner surface of the second portion of the chamber 32, either on the front plate 16, or the back plate 14. With this arrangement, the coupler 66 can extend either to the inner surface of the flange 18, or straight across the width of the second portion of chamber 32.

Figure 2:
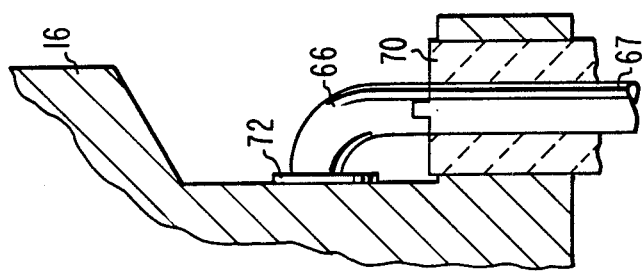
FIG. 2 is an enlarged view of an alternative form of the coupling loop for coupling the energy into the cavity.

FIG. 2 shows an alternative arrangement of the coupler 66 and the front plate 16. A thin insulator disk 72 is fixed in place between the end of the coupler 66 and the front plate 16. The diameter of the disk 72 is at least 30% larger than the diameter of the coupler wire. The thickness and dielectric constant of the disk 72 are chosen to give a value of the capacitance between the coupler 66 and the front plate 16 to compensate for the series inductance of the coupler 66.

The following Table shows typical dimensions for a cavity 10 of the present invention which have been found suitable for operation at 2450 MHz and with the coaxial section having an impedance of 50 ohms.

TABLE I

| | |
|---|---|
| Outer diameter of chamber 26 | 68.3 mm |
| Width of chamber in second portion 32 | 12.9 mm |
| Top diameter of hub 20 | 17.9 mm |
| Bottom diameter of hub 20 | 27.8 mm |
| Width of chamber in first portion 30 | 4.2 mm |
| Outer diameter of tube 34 | 3.0 mm |
| Inner diameter of tube 34 | 2.0 mm |
| Length of coupler 66 | 10.0 m |
| Height of coupler 66 | 4.8 mm |
| Diameter of coupler | 3.2 mm |
| Diameter of central conductor wire 67 | 3.2 mm |
| Diameter of hole 68 | 9.5 mm |
| Dielectric constant of insulator 70 | 2.1 |

Figure 3:
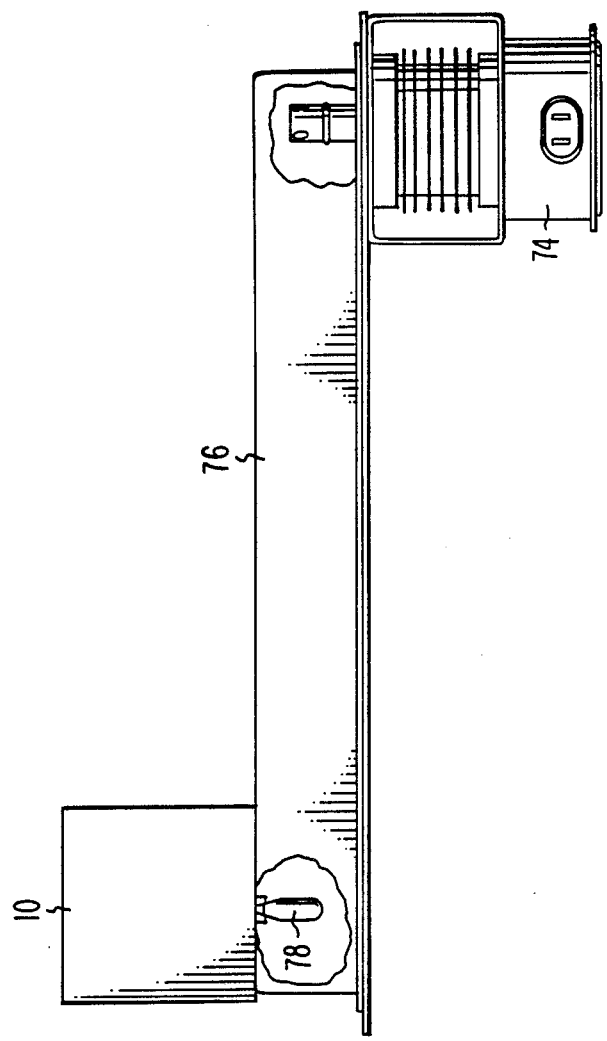
FIG. 3 is a schematic view of a system in which the cavity is connected to a power source.

The coupler 66, in combination with central conductor wire 67, extends out of the housing 12 and is connected to a source of microwave power. Referring to FIG. 3, there is shown one manner of connecting the microwave cavity 10 to magnetron power source 74. The microwave cavity 10 is mounted at one end of a waveguide 76 formed by an elongated aluminum box. The coupler 66, through central conductor wire 67, is connected to a metal antenna 78 which extends into the waveguide 76. The magnetron 74 is mounted at the other end of the waveguide 76, and is spaced from the end of the waveguide 76 a distance so that it is impedance-matched to the waveguide. However, instead of using a waveguide for connecting the coupler 66 to the power source, a coaxial cable can be used.

In the operation of the resonant cavity 10 of the present invention, a gas, such as helium, containing the material to be examined or measured is fed into the tube 34 where is passes through the first portion 30 of the chamber 26. A high frequency electromagnetic radiation, microwave power, is delivered to the chamber 26 by the coupler 66. A spark delivered by the ignition wire 62 lights the gas so as to generate a gaseous plasma in the tube 34. The plasma excites the atoms of the material to be examined or measured causing the atoms to emit light. This light can be seen through the window 56 and can be examined or measured by suitable instrumentation. Gases flowing from the end 36 of the tube 34 passes into and is collected in the exhaust chamber 48. The gases then flow out of the exhaust chamber 48 through the exhaust opening 52 and exhaust tube 54. The exhaust chamber 48 serves to prevent significant back diffusion of air into the plasma in the tube 34.

In prior art resonant cavities, the portion of the tube in the cavity is relatively long and some of the atoms to be examined are lost by reacting with the walls of the tube. Thus, these atoms cannot contribute to the generation of light. However, in the cavity 10 of the present invention, the width of the first portion 30 is made small so that only a short portion of the tube 34 is within the chamber 26 and exposed to the microwave energy. Thus, the atoms being examined are subjected to a much shorter length of the plasma and are thereby less likely to be absorbed by the wall of the tube. However, in the cavity 10 of the present invention, the second portion 32 of the chamber 26 is wider so that it can easily accommodate the coupler 66 or other power feed structure so that the microwave power can be readily provided to the chamber 26.

Another advantage of a narrower first portion 30 which contains the plasma is that the impedance of the narrow plasma is considerably decreased. This results in an increase in power density which provides a brighter plasma. For spectroscopy, the brighter plasma is often advantageous. Also, the concentration of the power in a shorter length of the tube results in an increase in the brightness of the light output making the examination or measurement of the light much easier.

By making the coupler 66 relatively thick, at least 3 mm in diameter for a 12 mm width cavity operating at 2450 MHz, the impedance of the coupler in combinations with the load represented by the cavity, can be made to approach the characteristic impedance of the coaxial conductor, which is generally at 50 ohms. However, wire diameters of greater than 3 mm provide improved operation with a wire diameter of about 5 mm being found to provide highly satisfactory operation. Also the insulating disc 72 placed between the end of the coupler 66 and the front plate 16, as shown in FIG. 2, forms a capacitor which reduces the bad effects of the self inductance of the loop.

Another advantage of the resonant cavity 10 of the present invention is that it does not require a tuner. If the Q of both the cavity and the coupling loop are both lowered, there is less need to tune. The cavity is lowered in Q by the increase in conductance of the plasma because of the shorter plasma. The Q of the coupling loop is lower due to the reduction of the reactance of the coupler 66. In view of the reductions in Q, and the greater power coupling, it has been found that a microwave tuner is not needed for routine use of the cavity 1? of the present invention.

Figure 4:
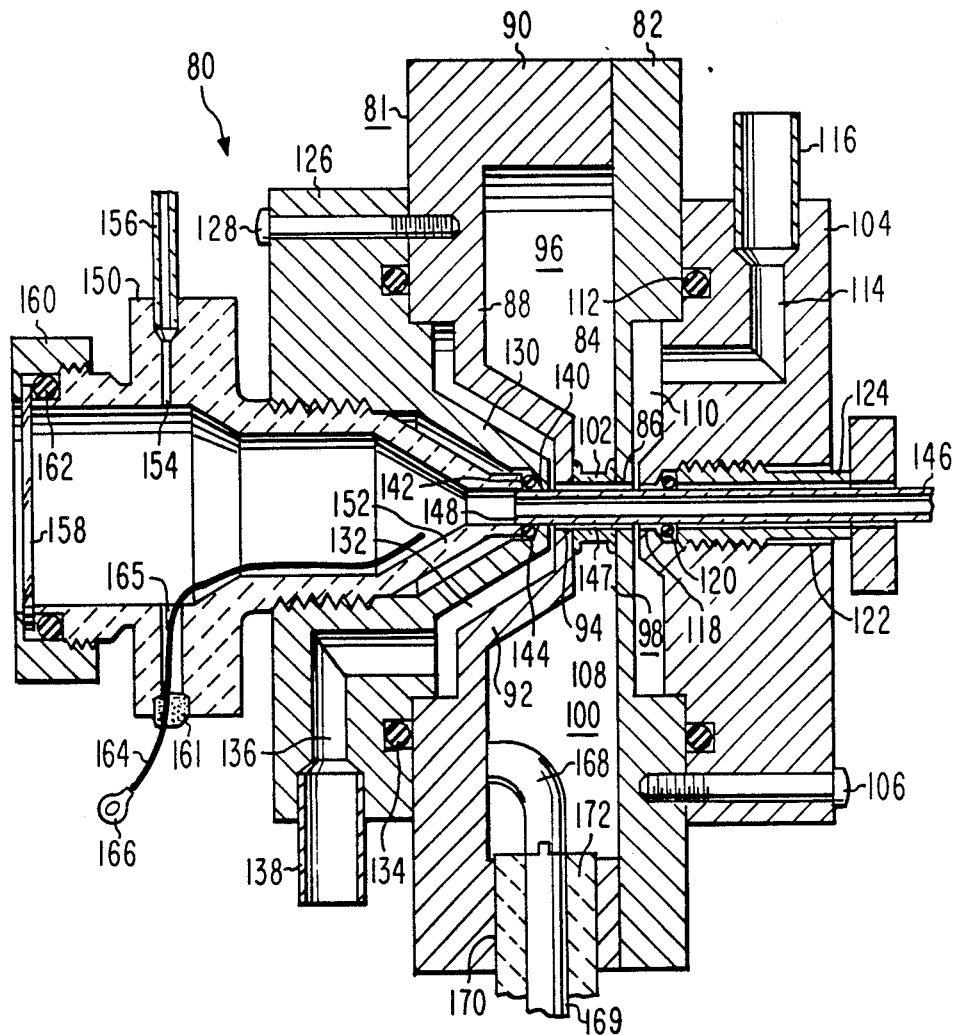
FIG. 4 is a sectional view of another form of the resonant cavity for use in optical spectrometry.

Referring to FIG. 4, a liquid cooled modification of the resonant cavity of the present invention is generally designated as 80. The liquid cooled resonant cavity 80 permits higher power levels than the resonant cavity 10 shown in FIG. 1. The resonant cavity 80 includes a housing 81 form of a flat back plate 82 having a central recess 84 in its outer surface and a opening 86 extending through the center of the bottom of the recess 84. A circular front plate 88 has an annular flange 90 around its periphery extending toward and engaging the back plate 82. The front plate 88 is secured to the back plate 82 in the same manner as described with regard to the cavity 10. The front plate 88 has a central hub 92 projecting toward but spaced from the back plate 82. The hub 92 has a central opening 94 therethrough which is in alignment with the opening 86 in the back plate 82. The back plate 82 and front plate 88 form a chamber 96 therein with the back plate 82 and front plate 88 being the sides of the chamber and the flange 90 being the outer wall of the chamber. The chamber 96 has a first portion 98 adjacent and around the openings 86 and 94 which is narrower between the sides than a second portion 100 which is around the first portion 98.

A non-metallic tube 102 is within the first portion 98 of the chamber 96 with the longitudinal axis of the tube 102 being in alignment with the longitudinal axes of the openings 86 and 94. The tube 102 is of a length to extend between the back plate 82 and the hub 92 and is sealed thereto. The inner diameter of the tube 102 is at least as large as the diameter of the openings 86 and 94. The tube 102 is made of material which has a low absorptivity for microwave energy, such as fused silica.

A first cooling plate 104 is mounted on the outer surface of the back plate 82 and is secured thereto by bolts 106. The cooling plate 104 has a central hub 108 fitting into the recess 84 in the back plate 82 but being spaced from the bottom of the recess to form a cooling cavity 110 therein. An annular sealing ring 112 between the cooling plate 104 and the back plate 82 seals the cooling cavity 110. An inlet passage 114 extends through the cooling plate 104 to the cooling cavity 110 and an inlet pipe 116 is connected to the inlet passage 114. An opening 118 extends through the center of the cooling plate 104 and is in alignment with the opening 86 in the back plate 82. A sealing ring 120 is in a recess 122 around the opening 118 and a annular nut 124 is threaded into the recess 122 and presses against the sealing ring 120.

A second cooling plate 126 is mounted on the outer surface of the front plate 88 and is secured thereto by bolts 128. The second cooling plate 126 has a hub 130 extending into the hub 92 of the front plate 88 but is spaced from the outer surface of the hub 92 so as to form a cooling cavity 132 therebetween. An annular sealing ring 134 is between the second cooling plate 126 and the front plate 88 to seal the cooling cavity 132. An outlet passage 136 extends through the second cooling plate 126 from the cooling cavity 132 to the periphery of the cooling plate 126 and an outlet pipe 138 is connected to the outlet passage 136. The hub 130 of the second cooling plate 126 has a central opening 140 therethrough which is in alignment with the opening 94 in the hub 92 of the front plate 88. An annular sealing ring 142 is in a recess 144 around the opening 140.

The cooling plates 104 and 126 are electrically conductive, and in close electrical contact with the back plate 82 and front plate 88 respectively. This prevents the unwanted escape of stray electromagnetic energy from the cavity through the cooling passages, as has been disclosed in U.S. Pat. No. 4,654,504.

An elongated refractory tube 146, similar to the tube 34 in the cavity 10 shown in FIG. 1, extends through the aligned openings 118, 86, 94 and 140 in the first cooling plate 104, back plate 82, front plate 88 and second cooling plate 126 respectively and the tube 102. One end 148 of the tube 146 projects slightly beyond the opening 140 in the second cooling plate 126. The other end of the tube 146, not shown, is connected to a source of gas which will form the plasma. The outer diameter of the tube 146 is slightly smaller than the diameter of the openings 86 and 94 and the tube 102 so that a passage 147 is provided between the tube 146 and the various openings and the tube 102 for the flow of cooling liquid from the cooling cavity 110 to the cooling cavity 132. The nut 124 presses the sealing ring 120 against the tube 146 and the sealing ring 142 is pressed against the tube 146 so as to seal the ends of the cooling passage along the tube 146.

A cylindrical exhaust chamber 150 of an electrical insulating material extends and is threaded into the hub 130 of the second cooling plate 126. One end 152 of the exhaust chamber 150 fits into the recess 144 and presses the sealing ring 140 against the tube 146. An exhaust passage 154 extends through the exhaust chamber 150 and an exhaust tube 156 is connected to the exhaust passage 154. A glass window 158 extends across the other end of the exhaust chamber 150 and is secured thereto by an threaded ring 160. A sealing ring 162 is provided between the window 158, exhaust chamber 150 and ring 160. An ignition wire 164 extends into the exhaust chamber 150 through a passage 165 therein which is sealed by a sealing material 167. The end of the wire 164 within the exhaust chamber 150 is adjacent the end 148 of the tube 146. The end of the wire 164 outside the exhaust chamber 150 has a terminal connector 166 thereon.

A coupler 168, similar to the coupler 66 in the cavity 10 shown in FIG. 1, is within the chamber 96. The coupler 168 is connected to a coaxial connector which includes a wire 169 extending through an opening 170 in the flange 90 of the front plate 88. The coupler 168 has an end engaging the inner surface of one of the wall of the chamber 96, such as the inner surface of the front plate 88. An insulator 172 is within the opening 170 and around the connector wire 169. Thus, the connector wire 169, insulator 172 and wall of the opening 170 form a coaxial conductor. The outer end of the coaxial connector wire 169 is connected to means for connecting the coupler 168 to a source of microwave power.

The resonant cavity 80 operates in the same manner as previously described with regard to the cavity 10 shown in FIG. 1. However, in the cavity 80 a flow of cooling liquid, such as water, is provided through the cavity. The liquid enters through the inlet pipe 116 and flows through the inlet passage 114 to the cooling chamber 110. The liquid then flows along the passage 147 around the tube 146 to the cooling chamber 132. From the cooling chamber 132, the liquid flows through the exhaust passage 136 and out through the exhaust pipe 138. As previously stated, this flow of cooling liquid through the cavity 80 permits the cavity to operate at high power levels. Instead of a cooling liquid, a cooling gas, such as air, may be used to cool the cavity.

The following Table shows typical dimensions for a cavity 80 of the present invention which have been found suitable for operation at 2450 MHz, using water as a cooling liquid, and with the coaxial section having an impedance of 50 ohms.

TABLE II

| Outer diameter of chamber 96 | 63.9 mm |
| --- | --- |
| Width of chamber in second portion 100 | 12.9 mm |
| Top diameter of hub 92 | 16.7 mm |
| Bottom diameter of hub 92 | 26.1 mm |
| Width of chamber in first portion 98 | 3.9 mm |
| Outer diameter of tube 146 | 3.0 mm |
| Inner diameter of tube 146 | 2.0 mm |
| Outer diameter of tube 102 | 4.8 mm |
| Inner diameter of tube 102 | 3.2 mm |

Figure 5:
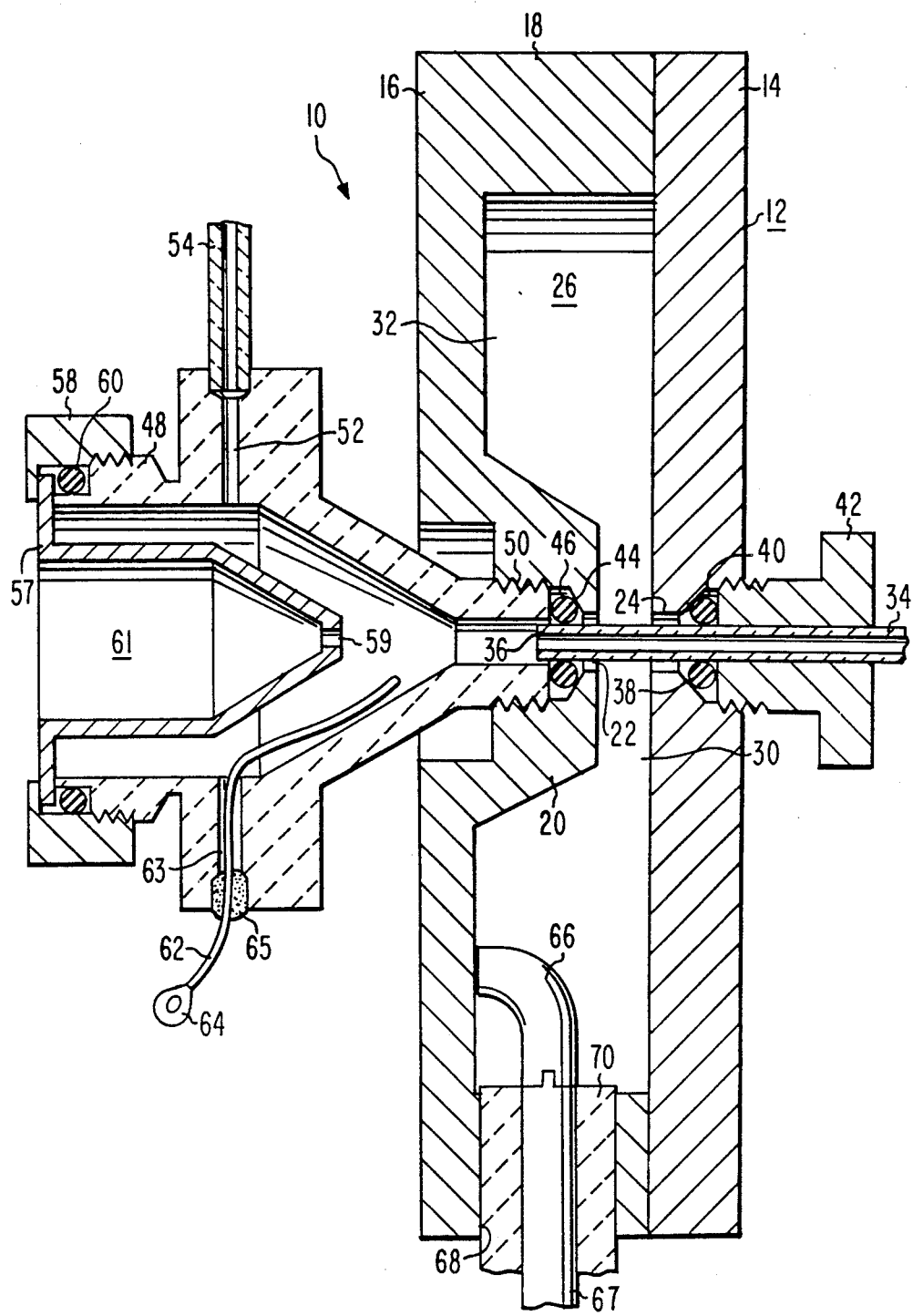
FIG. 5 is a sectional view of the resonant cavity shown in FIG. 1 but used for mass spectrometry.

Although the microwave cavities 10 and 80 are shown in FIGS. 1 and 4 and have been described as having windows 56 and 158 for use in optical spectrometry, they can also be used for mass spectrometry. Referring to FIG. 5, there is shown the microwave cavity 10 with the window 56 removed and with a sampling plate 57 mounted in the exhaust chamber 48. The sampling plate 57 contains an orifice 59 which communicates with the low pressure region 61 of a mass spectrometer interface. A portion of the exhaust gas from the plasma flows supersonically through the orifice 59, drawn by the low pressure of the mass spectrometer interface. The sampling plate 57 and orifice 59 are part of an interface between a plasma and a mass spectrometer. The construction and operation of such interfaces are well known and can be of the type shown and described in the previously referred to article of R. D. Satzger et al. The microwave cavity 80 shown in FIG. 4 may likewise be used in mass spectrometry by removing the window 158 and inserting a sampling plate which is designed to communicate with a mass spectrometer interface.

Thus, there is provided by the present invention a resonant microwave cavity for use with a gaseous plasma wherein the gaseous plasma is very short in length. This provides for a minimum of loss of the gas being absorbed into the hot wall of the tube and provides therefore a more efficient light source. Also it provides for a brighter light for easier measurement of the light. In addition the cavity of the present invention requires no tuner and is more stable during operation.

What is claimed is:

1. A resonant cavity for high frequency electromagnetic radiation used to excite a gaseous plasma comprising:
    a housing having fixed, spaced side walls and an outer wall forming a cylindrical chamber having an axis extending through said side walls, the chamber having a first portion adjacent and around the axis which is narrower between the side walls than a second portion of the chamber which is connected to and surrounds the first portion;
    a refractory tube extending along said axis of the chamber and through said side walls, said tube adapted to contain a gaseous plasma and having an open end to exhaust gases; and
    loop means coupled to the inner surface of a wall of the housing within the chamber including a wire having one end adjacent to the inner surface of the wall and its other end connected to a coaxial connector extending through an opening in the outer wall of the housing for coupling a high frequency electromagnetic radiation into said chamber,
    whereby the introduction of said electromagnetic radiation into said chamber initiates a gaseous plasma, said plasma remaining stable during subsequent operation.

2. A resonant cavity in accordance with claim 1 in which the outer diameter of the cylindrical chamber is much greater than the width between the side walls of the second portion of the chamber.

3. A resonant cavity in accordance with claim 2 in which the width of the first portion of the chamber is no greater than one-half the width of the second portion.

4. A resonant cavity in accordance with claim 1 in which the coaxial connector includes a central wire and an insulator around the wire where it passes through the outer wall so that the wire, insulator and outer wall form a transmission line.

5. A resonant cavity in accordance with claim 4 including means on the end of the connector wire outside the housing for connecting the loop to a source of microwave energy.

6. A resonant cavity in accordance with claim 1 including an insulator between the inner surface of the wall and the one end of the coupling loop wire.

7. A resonant cavity in accordance with claim 1 in which one end of the refractory tube is adjacent the outer surface of one of the walls of the housing.

8. A resonant cavity in accordance with claim 7 including an exhaust chamber mounted on said one wall of the housing with said one end of the refractory tube extending into said exhaust chamber, the exhaust chamber having an exhaust passage extending therethrough to permit gas in the chamber to exhaust therefrom.

9. A resonant cavity in accordance with claim 8 in which said exhaust chamber has a transparent window through which the end of the refractory tube can be viewed.

10. A resonant cavity in accordance with claim 8 including means extending into the exhaust chamber for extracting a portion of the plasma effluent from the end of the refractory tube into a mass spectrometer.

11. A resonant cavity in accordance with claim 8 including a spark wire extending through the exhaust chamber with one end of the wire being adjacent the end of the refractory tube.

12. A resonant cavity in accordance with claim 11 in which the exhaust chamber is cylindrical with the refractory tube extending into one end thereof, the window being across the other end and the exhaust passage extending radially therethrough.

13. A resonant cavity in accordance with claim 1 including means forming a cooling passage around the portion of the refractory tube that passes through the chamber to allow a cooling material to flow over and around said tube.

14. A resonant cavity for high frequency electromagnetic radiation used to excite a gaseous plasma comprising:
    a housing having a back plate and a front plate forming side walls spaced apart a fixed distance, said front plate having an annular flange wall, said side walls forming a cylindrical chamber having an axis extending through the side walls, said front plate having a hub projecting toward but fixedly spaced from the back plate, the hub and back plate having axially aligned openings therethrough along said axis of the chamber, the hub and back plate forming a first portion of the chamber which is narrower in a fixed dimension between the side walls than the remaining space of the chamber around the hub which forms a second portion of the chamber;
    a refractory tube extending along said axis of the chamber and through said side walls, said tube adapted to contain a gaseous plasma and having an open end to exhaust gases; and
    loop means coupled to the inner surface of a wall of the housing within the second portion of the chamber for coupling a high frequency electromagnetic radiation into said chamber,
    whereby the introduction of said electromagnetic radiation into said chamber initiates a gaseous plasma, said plasma remaining stable during subsequent operation.

15. A resonant cavity in accordance with claim 14 in which the means coupled to the inner surface of a wall is a loop including a wire having one end adjacent to the inner surface of one of said plate in the second portion of the chamber and the other end connected to a coaxial connector extending through an opening in the outer wall of the housing.

16. A resonant cavity in accordance with claim 15 in which the wire has a diameter of at least one quarter of the width of the second portion of the housing.

17. A resonant cavity in accordance with claim 15 in which the coaxial connector includes a wire extending through the opening in the outer wall of the housing and an annular insulator around said wire between the wire and the opening so that the wire, insulator and wall of the opening form a transmission line.

18. A resonant cavity in accordance with claim 17 including a cylindrical exhaust chamber mounted on said front plate with one end of the exhaust chamber extending to the hub and being aligned with the opening in the hub, said refractory tube having one end extending into the exhaust chamber.

19. A resonant cavity in accordance with claim 18 in which the exhaust chamber has a window secured across the other end through which the end of the refractory tube can be viewed, an exhaust passage extending radially therethrough to exhaust gas from the exhaust chamber, and a spark wire extending therethrough with an end of the wire being adjacent the end of the refractory tube.

20. A resonant cavity in accordance with claims 18 including means extending into the exhaust chamber for drawing a portion of the plasma effluent emitted from the refractory tube into a mass spectrometer.

21. A resonant cavity in accordance with claim 15 including a cooling tube within the first portion of the chamber and around said refractory tube, said cooling tube forming a cooling passage around and along said refractory tube within said chamber, a first cooling plate secured to the back wall and forming a cooling chamber therebetween, an inlet passage through said first cooling plate to said cooling chamber, and a second cooling plate secured to the front plate and forming a cooling chamber therebetween, an outlet passage extending through the second cooling plate from the cooling chamber, said cooling passage around the refractory tube being connected to said cooling chambers.

22. A resonant cavity in accordance with claim 15 including a waveguide, said resonant cavity being mounted on said waveguide, means connected to the coaxial connector wire which extends out of said housing for electrically coupling the loop to said waveguide and a magnetron power source mounted on said waveguide for providing high frequency electromagnetic radiation to said cavity.

23. A resonant cavity in accordance with claim 1 in which the wire has a diameter of at least one quarter of the width of the second portion of the housing.

24. A resonant cavity for high frequency electromagnetic radiation used to excite a gaseous plasma comprising:
a housing forming a chamber having fixedly spaced apart side walls and having a first portion and a second portion coupled to said first portion;
a refractory tube adapted to contain a gaseous plasma extending through said first portion and having an open end to allow a flow of gas therethrough; and
means coupled to the second portion of said chamber for coupling high frequency electromagnetic radiation into said chamber, wherein the overall length of the portion of said refractory tube exposed to the first portion of the chamber is less than the fixed dimension between said sidewalls in the second portion in a direction substantially parallel with the direction that said tube extends through said first portion,
whereby the introduction of said electromagnetic radiation into said chamber initiates a gaseous plasma, said plasma remaining stable during subsequent operation.

25. A resonant cavity in accordance with claim 24 including an exhaust chamber mounted on said one wall of the housing with one end of the refractory tube extending into said exhaust chamber, said exhaust chamber having an exhaust passage extending therethrough to permit gas in the chamber to exhaust therefrom.

26. A resonant cavity in accordance with claim 25 in which said exhaust chamber has a transparent window through which the end of the refractory tube can be viewed.

27. A resonant cavity in accordance with claim 25 including means extending into the exhaust chamber for drawing a portion of the plasma effluent from the refractory tube into a mass spectrometer.

28. A resonant cavity in accordance with claim 25 including a spark wire extending through the exhaust chamber with one of the wire being adjacent to the end of the refractory tube.

29. A resonant cavity in accordance with claims 28 in which the exhaust chamber is cylindrical with the refractory tube extending into one end thereof, a window extends across the other end and the exhaust passage extending radially therethrough.

30. A resonant cavity in accordance with claims 24 including means forming a cooling passage around a portion of the refractory tube that passes through the chamber to allow a cooling material to flow over and around said tube.

* * * * *